(12) United States Patent
Marian

(10) Patent No.: US 6,837,853 B2
(45) Date of Patent: Jan. 4, 2005

(54) SYSTEM AND METHOD FOR USING AN ULTRASOUND TRANSDUCER WITH AN INTEGRATED TRANSDUCER INFORMATION SYSTEM

(75) Inventor: Vaughn Marian, Saratoga, CA (US)

(73) Assignee: Acuson Corporation, Mountain View, CA (US)

(*) Notice: Subject to any disclaimer, the term of this patent is extended or adjusted under 35 U.S.C. 154(b) by 0 days.

(21) Appl. No.: 10/185,217

(22) Filed: Jun. 27, 2002

(65) Prior Publication Data

US 2004/0002657 A1 Jan. 1, 2004

(51) Int. Cl.[7] ................................................. A61B 8/00
(52) U.S. Cl. ...................................... 600/437; 600/459
(58) Field of Search ............................... 600/407–472; 367/7, 11, 130, 138; 73/595–630; 128/916

(56) References Cited

U.S. PATENT DOCUMENTS

| | | | |
|---|---|---|---|
| 5,520,187 A | 5/1996 | Synder | 128/661.01 |
| 5,590,658 A | 1/1997 | Chiang et al. | 128/661.01 |
| 5,603,323 A | 2/1997 | Pflugrath et al. | 128/660.01 |
| 6,126,608 A | * 10/2000 | Kemme et al. | 600/459 |
| 6,241,673 B1 | 6/2001 | Williams | 600/437 |

* cited by examiner

*Primary Examiner*—Ali M. Imam

(57) ABSTRACT

The present invention is an ultrasound imaging system comprising a transducer assembly having a scan-head, a non-volatile means for storing data related to transducer usage, user comments, technical support, maintenace of the transducer assembly, operational imaging system software for at least one imaging system, transducer assembly identification, and settings of an ultrasound imaging apparatus coupled with the transducer assembly. The transducer assembly and ultrasound imaging apparatus may commuicate with each other.

23 Claims, 4 Drawing Sheets

SYSTEM AND METHOD FOR USING AN ULTRASOUND TRANSDUCER WITH AN INTEGRATED TRANSDUCER INFORMATION SYSTEM

FIELD OF THE INVENTION

This invention relates to ultrasound phased array imaging systems used for diagnostic medical procedures. More specifically, this invention relates to the operating software required to adapt and optimize a general purpose imaging system to specific transducers based on large arrays of piezo-electric transceivers.

BACKGROUND OF THE INVENTION

Ultrasonic imaging systems are used to acquire real-time images of the interior of the body by using a transducer incorporating a linear array of piezo-electric elements. Modern imaging systems use a multitude of independent transmitters, each electrically connected to an corresponding piezo-electric element within the transducer. By controlling the phase relationships between the transmit pulses from the multitude of elements, ultrasound energy can be directed to predetermined areas within the body. Similarly, a multitude of independent receivers within the imaging system, each connected to the individual elements of the array, are used to interpret relatively small electrical signals resulting from sound energy impinging on the elements after being reflected from internal structures within the body.

Different transducers are required to fulfill a broad range of diagnostic needs. For instance, small, shallow structures generally are best imaged using a high frequency transducer with a relatively small size. Although this type of transducer inherently provides excellent resolution of the finest details, it has limited ability to view deeper structures within the body. Larger organs, deep within the body, i.e. the heart, are best imaged with lower frequency transducers because of the diminished attenuative losses of low frequency ultrasound energy. These transducers must be relatively small because they must acquire an image through the limited space between the ribs. Obstetric transducers generally are of low frequency but are physically large so that they can get a good view of a large part of the fetus.

One imaging system must support a wide range of transducers. Modern imaging systems use relatively complex programmable digital logic to cause the transducer to transmit ultrasound energy into the body, to receive and interpret the relatively small received signals, and to generate a diagnostically usable image on a display device. Software, customized to the requirements of a particular transducer, must be available to the imaging system to enable it to acquire and display the optimum image for that device. Generally, the current practice is to pre-install the appropriate operating software for each transducer to be used with the imaging system into that system. Thus, before the imaging system can be used, it must determine what transducer will be used; this is generally done by electronically interrogating an identification code that has been factory installed within the transducer. Upon identification of the transducer, it selects from its software library, or archive, the program that is required to support that device. This operating software or micro-code is used to preset programmable logic within the imaging system to parameters optimum for the transducer. Electronic logic controlling the transmitters, the receivers, and the display system are preset during this initialization process.

SUMMARY OF THE INVENTION

The present invention is an ultrasound imaging system comprising a transducer assembly having a scan-head, a non-volatile means for storing data related to transducer usage, user comments, technical support, maintenace of the transducer assembly, operational imaging system software for at least one imaging system, transducer assembly identification, and settings of an ultrasound imaging apparatus coupled with the transducer assembly. The transducer assembly and ultrasound imaging apparatus may commuicate with each other.

Furthermore, the present invention is a method of operating a transducer assembly to process usage data of the transducer assembly, the method comprising the steps of inputting transducer usage data into an ultrasound imaging system coupled with the transducer assembly, wherein the ultrasound imaging system is located in a first location, transmitting the transducer usage data to at least a second location, using the transducer usage data to determine cost data of the usage of the transducer assembly, and transmitting the cost data to the first location.

BRIEF DESCRIPTION OF THE DRAWINGS

Corresponding reference characters indicate corresponding parts throughout the several views of the drawings.

DETAILED DESCRIPTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail. U.S. patent application Ser. No. 10/185,529 and U.S. patent application Ser. No. 10/185,472 filed on the same day as the present application are assigned to the assignee of the present invention and are hereby incorporated by reference.

Figure 1:
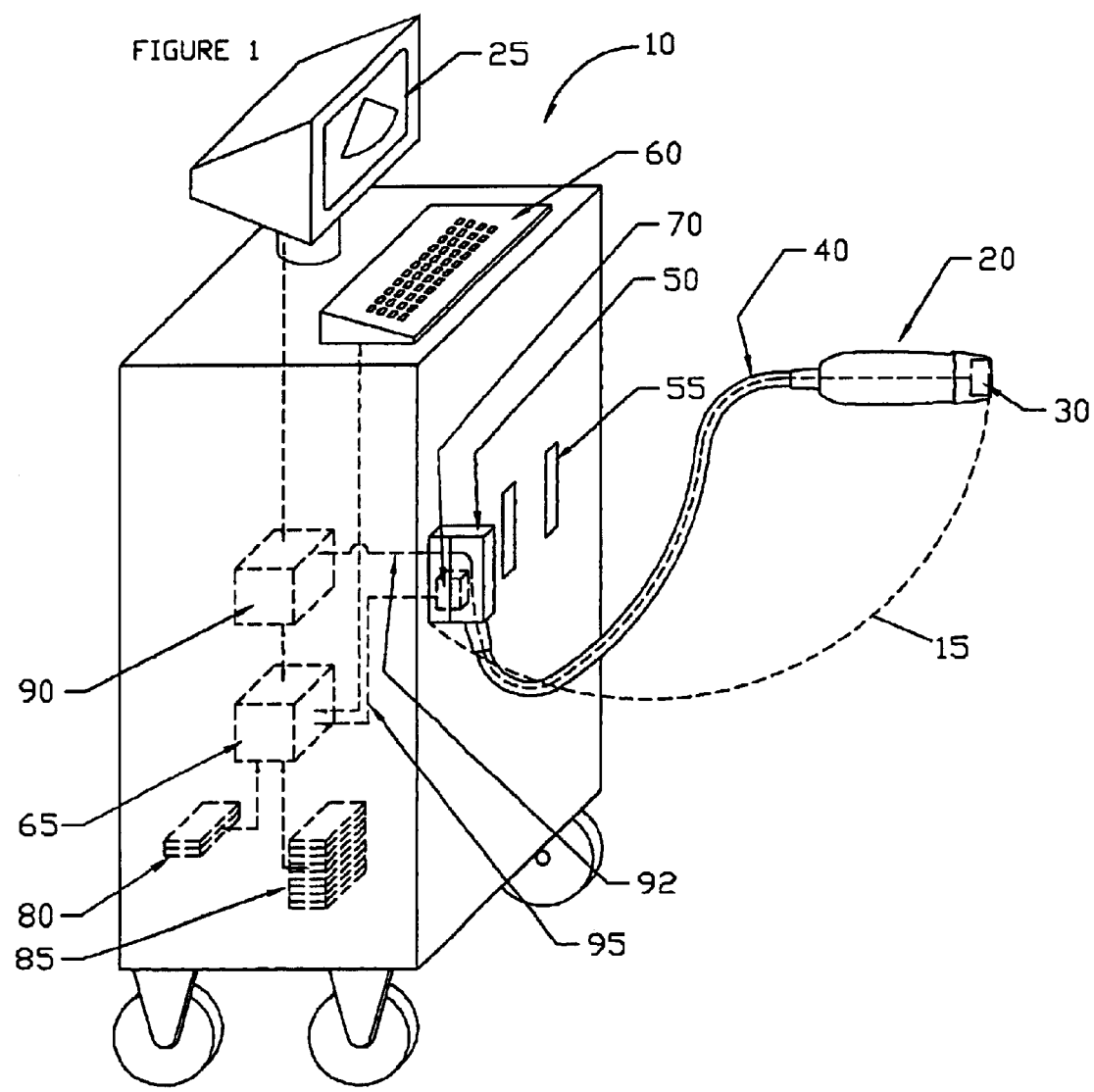
FIG. 1 shows an overall view of an ultrasound imaging system used for medical diagnostic procedures. Also illustrated is a block diagram of those systems used to interact with the invention.

FIG. 1 shows an ultrasound imaging system 10 for medical diagnostic procedures. The ultrasound imaging system 10 includes a transducer assembly 15 that consists of an scan head 20 incorporating an array of electrically and mechanically independent piezo-electric transceivers 30, a cable 40 consisting of a large number of coaxial conductors, and a connector 50, designed to reliably provide an electrical interconnect with the imaging system 10 and capable of being conveniently disengaged from that system, as required.

The imaging system 10 embodies all the electronic circuitry necessary for the scan head 20 to generate an ultrasound field within the patient's body, to intercept and interpret the energy reflected from the internal organs, and to display a graphical representation of the internal structures in a useful manner such as a monitor 25.

As stated previously, the wide range of possible diagnostic procedures require a diversity of transducer assemblies. Multiple receptacles 55 on the front or side panel of the imaging system 10 allow the system to be used with any of the attached transducer assemblies through use of internal switching circuitry (not illustrated). The operator may use a control device 60, such as, but not limited to, a keyboard to cause the imaging system 10 to switch to the desired transducer assembly. Numerous geometric and electrical characteristics are possible for different transducer assemblies. The imaging system controller 65 must know information such as distance between elements, sensitivity of each element, number of elements, the depth within the body at which energy is focused, etc. order to optimize the operation of the ultrasound transmitters, receivers, and image generating circuitry.

Typically, information about a particular transducer, in the form of micro-code, is stored in a non-volatile archive 85 within the imaging system. When the controller 65 is able to identify the transducer 20 that is to become active, it copies the appropriate micro-code set from the non-volatile archive 85 into a volatile memory 80. This micro-code set within the volatile memory 80 is then used by the controller 65 to optimize transmit and receive beam forming and image scan conversion circuitry 90 for use with the active transducer.

This invention relates to a Transducer Information System (hereinafter "TIS") 70 located within the connector 50 of the detachable transducer assembly, along with all the supporting circuitry and operational software within the imaging system to properly communicate and control the TIS. Transducers with the TIS are compatible with existing imaging systems as they incorporate the normal transducer identification features. To utilize the features of the TIS, the imaging system must be made compatible either during manufacture or during an upgrading process. Once compatible, the imaging system can use transducers with or without the TIS interchangeably. In additional to the normal analog signals 92 that are exchanged between the imaging system 10 and the transducer assembly 20, digital data can be exchanged with the TIS through circuitry 95 designed for that purpose.

Figure 2:
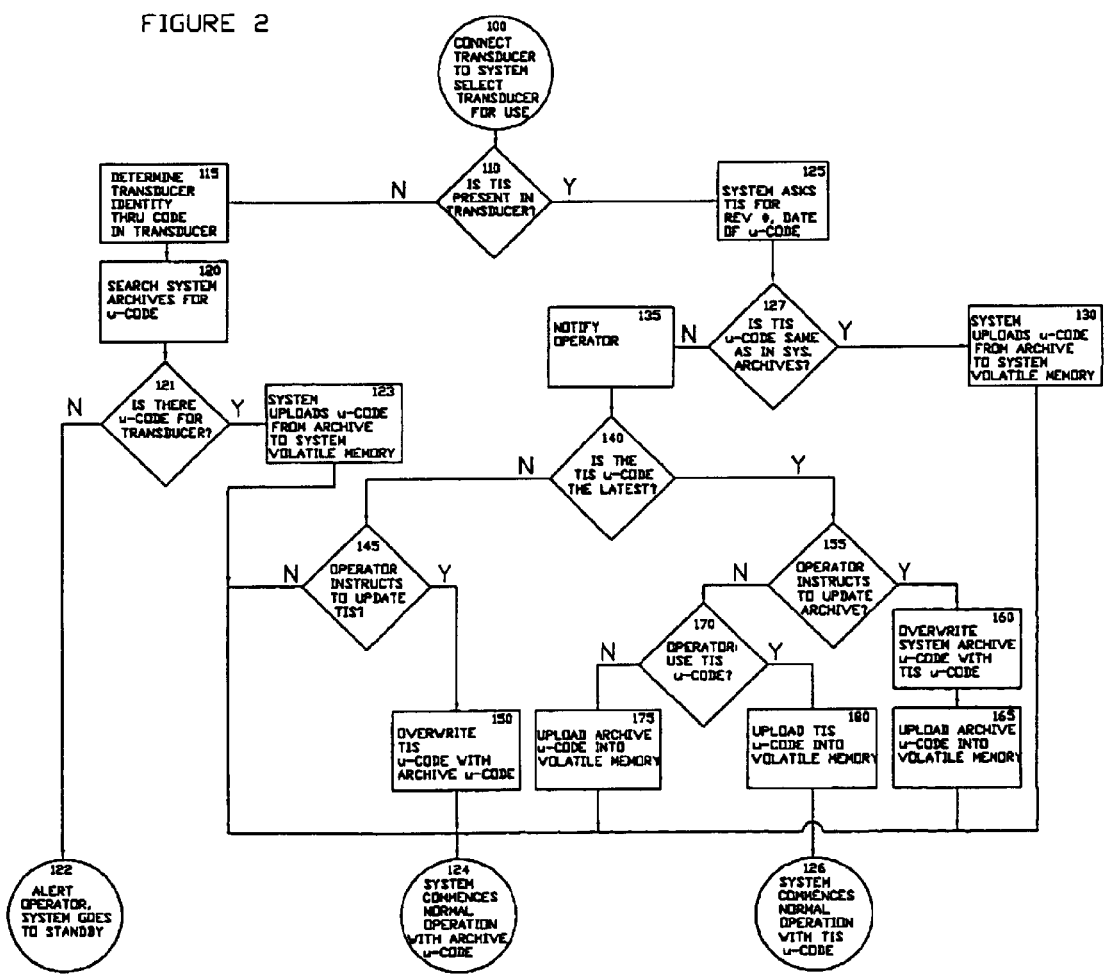
FIG. 2 shows a flow chart illustrating the usage of a Transducer Information System.

Referring to FIG. 2, the following sequence of events would typically occur before using a specific transducer assembly with a TIS. The operator selects the transducer to be used in the diagnostic procedure (step 100). The imaging system then connects the appropriate transducer receptacle to its internal electronic circuitry using either solid-state switches or mechanical relays (step 105). The imaging system then determines if the transducer assembly 15 has a TIS 70 (step 110). If it does not, the imaging system 10 attempts to identify the transducer through the normal identification code built into the transducer assembly (step 115). The imaging system then searches its archives for the appropriate micro-code (step 120). If the micro-code in the imaging system archive 85 is not present (step 121), the operator is alerted and the imaging system goes to standby (step 122). If the micro-code is present (step 121), The system commences normal operation with the archived micro-code (step 124).

If the transducer assembly has a TIS (step 110), the system finds and interrogates the TIS 70, for the revision and date of its integral micro-code set (step 125). If an identical set of micro-code already exists in the system's archives (step 127), the system uploads the system's micro-code set to the system's volatile random access memory (step 130), and initialization proceeds as outlined above. This eliminates delays associated with uploading the micro-code from the transducer assembly. But if identical micro-code is not found (step 127) in the system's archives, the operator is alerted on the display or other means (step 135).

If, when comparing the revision or date code of the micro-code sets, the archive is found to be the latest set, then the operator is asked if the TIS set should be updated (step 145). If the operator decides not to update the TIS, the system commences normal operation with the archive micro-code (step 124). But, if the operator decides to overwrite the older code on the TIS (step 150), this will be done by before or during normal operation (step 124).

If the TIS micro-code is the latest version (step 140), the operator is asked if the archive micro-code set should be updated with micro-code from the TIS (step 155). If the operator decides to update the archive micro-code, it will be overwritten by TIS micro-code (step 160). After uploading this newly updated archive micro-code into the volatile memory (step 165), the system will commence normal operation (step 124).

If the operator decides not to update the archive, (step 155), s/he will be asked to decide which micro-code set to use (step 170). If the older archived micro-code set is to be used, it will be loaded into volatile memory (step 175), and normal operation will commence (step 124). On the other hand, if the operator decides to use the later TIS revision of the micro-code, this set will be uploaded into the volatile memory (step 180) and the system will commence normal operation (step 126).

Figure 3:
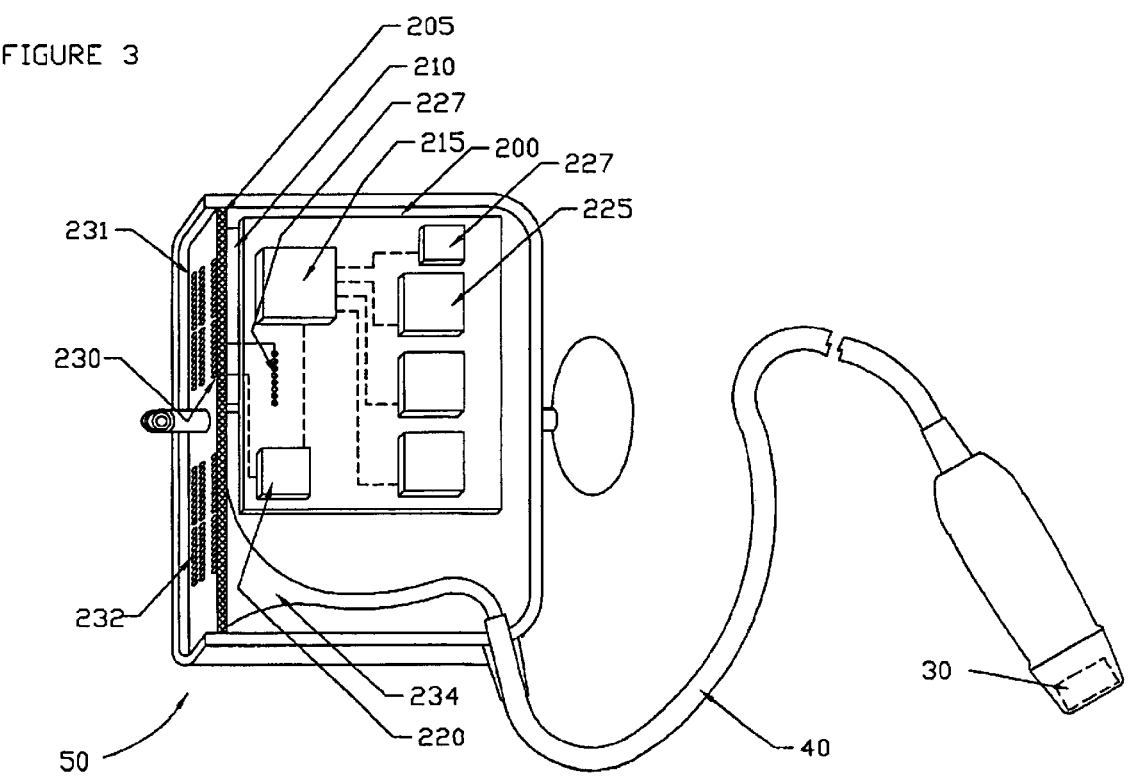
FIG. 3 shows a diagram of the Transducer Information System hardware.

FIG. 3 shows the removable transducer assembly with the TIS 70. With the exception of the TIS, all components illustrated are common to previous ultrasound transducer assemblies. The particular electrical connector illustrated is a "pinless" type used in the Acuson Sequoia imaging systems. The TIS my also be incorporated into "pin" type connectors, such as those based on ITT Canon "DL" type components.

The TIS is contained in a printed wiring board assembly 200 that interfaces electrically to the main board 205 of the pinless connector through a plug and receptacle assembly 210. The TIS contains logic devices for its various functions. A controller 215 coordinates all the required data transfer and memory read/write activities. A bi-directional communication device 220 is used to exchange data with a similar device in the imaging system. A non-volatile memory (i.e. flash memory) 225 system stores transducer data for use by the imaging system. Transducer identification code circuitry 227 is integrated into the TIS board assembly 200 to allow older imaging systems to use the newer transducers with a TIS system. An integrated circuit which may clock and calendar information 227 is optional.

The controller 215 can be a general-purpose microprocessor, a programmable gate array (PGA), or an application specific integrated circuit (ASIC). The use of digital circuitry within the system connector during the critical period when very low-level analog signals are being received and detected by the imaging system may create a radio frequency interference problem. To minimize this potential problem, one of ordinary skill in the art may make the digital circuitry within the transducer connector quiescent, under the control of the imaging system, during this critical receive phase of the imaging acquisition process.

The Intel "8051" is one example of a microprocessor that could be used as a controller in the TIS. Programmed instructions, stored in the non-volatile flash memory, microprocessor, or separate non-volatile memory device close to the microprocessor, adapt the microprocessor to perform the controller function required by the TIS.

The Xilinx "XC3042-100PQ100C" is one example of a programmable gate array (PGA) that may be used as a controller for the TIS. Generally, PGA's require a set of instructions be programmed into the device before they can be used for a specific application. This information may be stored in the imaging system and downloaded during the initialization sequence for the transducer assembly. Other similar devices are on the market that would be equally suitable for this application.

High density, low cost flash memory device(s) can store enormous amounts of digital data and are non-volatile thereby retaining data when power is removed (i.e. the transducer is removed from the imaging system). The amount of memory required for the micro-code storage feature of the TIS, may be between 1 and 10 million bytes. The Advanced Micro Devices part "AM 29LV640D" and the Intel part "28F64J3A" are examples of flash memory devices that may be used for this application. Other types of flash memory devices are available that have equivalent functionality. In this application, a set of micro-code is stored in this flash memory device(s) during the transducer assembly manufacturing process. This data may be changed or updated in the field by the operator using the supporting capabilities built into the imaging system. The TIS may also use "Read Only Memory" devices.

Bidirectional data communication between the TIS within the transducer assembly and the imaging system may be accomplished in several ways. One method uses at least two contact pads 230 in the connector/receptacle system to establish an electrical interconnection for serial data communication. Similar functionality could be achieved using a parallel data communication devices, but at the price of a higher number of required electrical interconnects. Standard communication protocols such as the Universal Serial Bus (USB) and Firewire have sufficient communication rates for this application. Alternatively, a dedicated proprietary serial channel communication system could be developed for this system to reduce the controller hardware requirements.

Wireless methods between the imaging system and the TIS may also be exploited for bidirectional data communication for this application. This would allow the imaging system, or to communicate with transducer assemblies that are not plugged into the system receptacles. Thus, the imaging system may determine which transducers were in the diagnostic room and may also investigate critical information on each of those it could communicate with, etc. In this way, data networks within the diagnostic facility could communicate directly to transducer assemblies not plugged into the imaging system.

One example of a wireless method is the use of infrared or visible light to establish the bi-directional communication link between the imaging system and the TIS. This technology has been used in consumer remote control devices. Such an interface may be a cost-effective method for upgrading older imaging systems to take advantage of newer transducer assemblies having a TIS. Accordingly, system receptacles would not need to be updated. A converter using an infrared transceiver may be mounted on the exterior of the imaging system or in any location within the diagnostic room having a line of sight to a similar transceiver on the system connector. Radio frequency wireless communication between the imaging system and the transducer assembly may be preferred in certain applications because of its ability to "see" around corners and through obstacles. A communication system, based on the "Blue-tooth" communication standard protocol, would be example of such a wireless data link.

Figure 4:
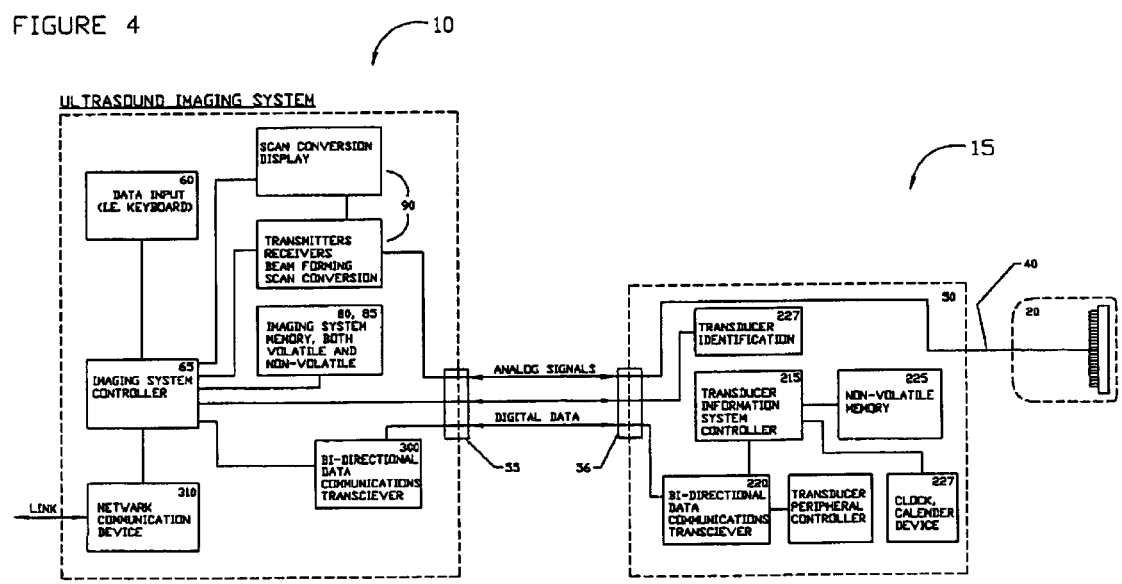
FIG. 4 illustrates an overall block diagram of the transducer assembly, the imaging system, and the network remote access communication link.

FIG. 4 is a block diagram of a transducer assembly with a transducer assembly having a TIS and an imaging system. The transducer assembly is detachable portable and may be detached from the imaging system through use of the connector system (receptacle on the imaging system 55, and a plug on the transducer assembly 56). The connector 50 provides an electrical interface between both the analog and digital circuitry of the imaging system 10 and the transducer assembly 15. Since the diagnostic system may exploit scan-heads with a large number of independent piezo-electric transceivers (linear or phased array devices), large numbers of electrical interconnections for the analog signals are made in the connector system. During the transmit phase, the interconnects transfer high voltage transmit pulses from the imaging system to the array of elements 30 within the scan-head 20. During the receive phase, the interconnects transfer very small signals, generated by the array of elements in the scan head upon intercepting ultrasound energy reflected from the internal organs of the body, to the imaging system with a minimum of degradation or noise injection.

Only minor hardware and software changes are required within the imaging system to support the TIS capable transducer assembly. In most cases only a bi-directional data communication device within the imaging system 300, electrically and operationally compatible with a similar device 220 in the TIS, is required to enable the imaging system controller 65 to transfer data to and from the transducer assembly. Numerous different hardware devices and communications protocols, as outlined above, exist to simplify the addition of these features to an imaging system.

Serial communication using a standard interface like Universal Serial Bus (USB), or "Firewire" is capable of moving data quickly between the system and the transducer assembly. Since the micro-code set may be between 1 and 10 megabytes in size, high-speed data communications reduce the time required to upload or download data. Serial communication links reduce the number of conductive links. Only two or three different and independent contact pads are required to support the digital data transfers using this method.

Optical methods (infra-red or optical light) may be used for the required communication link. Optical transceivers, located within in the connector system could be exploited to accomplish high-speed data transfers between the imaging system and the TIS. This method may be used when retrofitting the TIS capabilities to older imaging systems since altering the contact assignments within an existing connector system is a major undertaking. The optical transceivers could be retrofitted to an older system, remote from the transducer assembly receptacles. One may also incorporate both an optical and a wired communication link to the same transducer assembly.

Several classes of data may be archived within the non-volatile memory of the TIS within the transducer assembly. This data may be accessed or altered by the imaging system as a results of commands issued by the operator. A data network may also access or alter the data from remote locations. The data may include, but is not limited to, general transducer information, imaging system support micro-code required by the imaging system, transducer history information, and information required to document the transducer or imaging system usage.

General information about the transducer assembly may include, but is not limited to, the transducer information specific to one model or information specific to the particular transducer. The data may include, for example: the transducer model, the date of manufacture, the serial number, the refurbish status, etc. For data specific to a particular transducer, status flags may tell the TIS controller not to alter the data.

Imaging system support information includes all the micro-code required by the system to use the transducer assembly. Additional information, such as micro-code revision number, data of release, and an imaging system key that allows the system only to access micro-code that it can use, may also be included. Micro-code, specific to other types of imaging systems, may have its own key, specific to those systems. Thus, one self-contained transducer assembly could contain the operating micro-code unique to the requirements of a number of different imaging systems. Multiple micro-code sets, specific to one type of imaging system may be included. Multiple micro-code sets can be used for clinical comparative evaluation purposes during the transducer development process. Alternative micro-code sets for one type of imaging system could enable certain diagnostic capabilities, not needed or required for normal procedures to be available.

Micro-code data sets are highly dependent on the physical characteristics of a particular transducer, and reflect the results of experimental evaluations of imaging performance and ultrasonic power emission measurements. Not only does the micro-code optimize the diagnostic performance of the transducer assembly/imaging system, the micro-code also incorporates features that prevent the transducer from being operated in a manner that would exceed regulatory limits on ultrasonic power, designed to assure the safety to the patient. Generally, each different imaging system requires its own unique set of micro-code to operate one particular transducer.

Because of manufacturing variations, different transducers of the same model may not have identical performance. The micro-code stored in the TIS may be optimized to reflect the actual experimentally determined transducer characteristics instead of the average for a population for transducers. As a consequence, a transducer with a TIS may be operated at a power level closer to the regulatory limit. Increased transmit power generally results in better imaging resolution for better or quicker diagnosis of abnormalities when viewing organs or structures within the body, particularly at the greater depths.

Alternatively, the micro-code stored in the TIS may also reflect the results of measurements on large populations of transducer assemblies; this averaging of data from multiple transducers is a normal industry practice. While this method is quite cost effective because of the reduced testing requirements, each transducer will not be operated at its optimum level.

The micro-code may be changed over the life of a transducer assembly in order to improve diagnostic performance. The changes may reflect clinical trials conducted after the transducer was released to production or may reflect problems discovered in the field after the product was introduced. Presently, the micro-code is built into the imaging system and is not upgraded until a major revision is introduced for the system. Thus, improvements to the micro-code are unavailable during this period before the major system revision. The TIS provides a faster, more flexible method for updating the micro-code so that improved diagnostic performance may be exploited at an earlier date. Also, the introduction of new transducer assemblies no longer has to be delayed by field upgrade software schedules as the transducer assembly with a TIS is a self-sufficient entity.

Because the transducer becomes a self-contained, independent system, the imaging system does not have to be pre-programmed with an experimental micro-code set before clinical trials can be conducted. The numerous micro-code iterations common to the product development activities are much more convenient when the TIS is exploited.

Transducer history archiving within the TIS may be used for operational, problem diagnosis, and for business reasons. For example, the TIS may automatically document the date of use, the time of use, the power level that was used, and the imaging system with which the transducer assembly was used, and the operator's identification. The archived transducer history may also provide information useful to performing repairs, understanding transducer failures and evaluating operational factors that affect the product life and performance. This gathered information may be used to develop future products.

The imaging system may archive its most recent imaging system settings in the memory of the TIS. During future diagnostic procedures, the imaging system could use this data to automatically restore previous operational settings; this could significantly reduce the time to obtain a clinically useful image.

Transducer assemblies are evaluated periodically for imaging performance and safety. Thus, the archived transducer history may contain data related to scheduling this required maintenance. Transducers that are used frequently would be checked more often than those that are seldom used. This is likely to reduce service costs.

Other general information that could be archived in the TIS includes user comments, concerns, or observations, relevant to the transducer. The user may enter this information into the TIS by an input device such as, but not limited to, the imaging system keyboard. Other operators or service groups may use this information.

The TIS may be used to archive the results of periodic transducer diagnostic measurements. The measurements may include the results of imaging tests on a ultrasound phantoms or other tests designed to evaluate or predict the diagnostic effectiveness of the transducer. This provides base line data that is useful the next time the transducer is tested. Safety measurements, such as electrical insulation integrity tests, may also be archived in the TIS.

The TIS may archive information in the form of help files. For example, information such as telephone numbers or web sites for technical support may be included.

If the imaging system has a network communication device or link 310, the TIS may exploit this network link to allow access to the information stored within the transducer assembly from a remote location. Since ultrasound imaging systems generally exploit the capabilities of general-purpose programmable logic devices such as microprocessors, little or no hardware, beyond the bi-directional data communications link described above 300, would be required to support the TIS. Thus, operating system software for the imaging system may access the TIS.

To take one example, the network link between an imaging system and a remote location may be used in a transducer leasing and billing business model. The life span of a transducer assembly is dependent on the amount of its use. A facility may lease a transducer assembly and pay a monthly flat fee for the use of a leased transducer and additionally pay a fee based on the number of minutes that the transducer is used. Because the transducer usage data in the TIS is remotely accessible by the lessor, the lessor may bill the lessee based on this usage amount. Thus, billing may be based on a record of actual use in a manner similar to other services, such as electricity usage or telephone usage. The imaging system may also access the usage data from the TIS and calculate a running total for the transducer assembly lease to send to the remote location of the lessor. Using the archived data, leasing rates may be determined to reflect the way that the transducer is used.

Similar to the leasing model above, another method for using the network link is a method of tracking the usage of the transducer assembly so that a lessor or user is aware when routine maintenance of the transducer assembly is necessary. The data related to the amount of usage is sent to the lessor's location, and after a certain amount of usage, the lessor may send a serviceperson to perform routine maintenance on the transducer assembly or notify the lessee to perform maintenance, etc.

The following table contains examples of the type of data that may be stored in the non-volatile memory of the TIS:

| | |
|---|---|
| Transducer Information | Transducer identification information |
| | Date of microcode software release |
| Imaging System Support | Operational imaging system software for imaging system $n_1, n_2, n_3, \ldots$, revision number, date of release |
| Transducer History | Log of transducer usage, date, time, power level, imaging system results of transducer self test, date |
| | Log of operator usage |
| General Transducer Archive | User comments |
| | Image system settings from a prvious imaging session |
| | Results of periodic transducer self test |
| | Parameters for calculating user fees |
| | Websites for tech support, contact for lease support |

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. An ultrasound imaging system comprising:
   a transducer assembly having a scan-head, a non-volatile means for storing data related to at least one of the following:
   (a) transducer usage
   (b) user comments
   (c) technical support
   (d) maintenace of the transducer assembly
   (e) operational imaging system software for at least one imaging system
   (f) transducer assembly identification
   (g) settings of an ultrasound imaging apparatus coupled with the transducer assembly
   a means for communicating with the ultrasound imaging apparatus coupled with the transducer assembly; and
   the ultrasound imaging apparatus having a means for communicating with the transducer assembly.

2. The invention of claim 1 wherein the non-volatile means for storing data comprises a flash memory device.

3. The invention of claim 1 wherein the means for communicating with an ultrasound imaging apparatus coupled with the transducer assembly and the means for communicating with the transducer assembly are wireless.

4. The invention of claim 1, wherein the ultrasound imaging system further comprises an user input means for entering data into the non-volatile means for storing information.

5. The invention of claim 1, wherein the ultrasound imaging system further comprises means for accessing data stored in the non-volatile means for storing information.

6. The invention of claim 1, wherein the data comprises date-related imaging session information.

7. The invention of claim 1, wherein the data comprises power levels of the scan head.

8. The invention of claim 1, wherein the data comprises the duration of an imaging session.

9. The invention of claim 1, wherein the data comprises identification of the transducer assembly.

10. The invention of claim 1, wherein the data comprises the date of the operational imaging system software.

11. The invention of claim 1, wherein the data comprises patient identification.

12. The invention of claim 1, wherein the data comprises identification of operators of the transducer assembly or medical diagnostic ultrasound imaging system.

13. The invention of claim 1, wherein the data compromises electrical insulation integrity information.

14. The invention of claim 1, wherein the data comprises imaging quality.

15. The invention of claim 1, wherein the data comprises the amount of usage of the transducer system.

16. The invention of claim 1, wherein the data comprises the passage of a predetermined amount of time.

17. The invention of claim 1, wherein the data comprises the results of the periodic running of an operational test of the transducer system.

18. The invention of claim 1, wherein the data comprises comments regarding the transducer assembly.

19. The invention of claim 1, wherein the data comprises imaging system settings used with the transducer assembly in a previous imaging session.

20. A transducer assembly comprising:
   a scan-head;
   a non-volatile means for storing data related to at least one of the following:
   (a) transducer usage
   (b) user comments
   (c) technical support
   (d) maintenace of the transducer assembly
   (e) operational imaging system software for at least one imaging system
   (f) transducer assembly identification
   (g) settings of an ultrasound imaging apparatus coupled with the transducer assembly; and
   a means for communicating with the ultrasound imaging apparatus coupled with the transducer assembly.

21. An apparatus comprising an ultrasound imaging system and a transducer assembly coupled to the ultrasound imaging system, wherein:
   the transducer assembly comprises:
      a scan head,
      non-volatile means for storing data related to characteristics of the transducer assembly determined at the time of assembly, means for communicating the data to the ultrasound imaging system; and the ultrasound imaging system comprises:

means for receiving the data related to the characteristics of the transducer assembly determined at the time of assembly; and means for maximizing the performance of the transducer assembly based upon the data related to the characteristics of the transducer assembly determined at the time of assembly.

22. A method of operating a transducer assembly to process usage data of the transducer assembly, the method comprising the steps of:

Inputting transducer usage data into an ultrasound imaging system coupled with the transducer assembly, wherein the ultrasound imaging system is located in a first location;

transmitting the transducer usage data to at least a second location;

using the transducer usage data to determine cost data of the usage of the transducer assembly;

transmitting the cost data to the first location.

23. A method of operating a transducer assembly to process maintenance data of the transducer assembly, the method comprising the steps of:

inputting transducer usage data into an ultrasound imaging system coupled with the transducer assembly, wherein the ultrasound imaging system is located in a first location;

transmitting the transducer usage data to at least a second location;

using the transducer usage data to determine maintenance needs of the transducer assembly;

providing maintenance for the transducer assembly at the first location based upon the transducer usage data.

* * * * *